United States Patent [19]

Motte et al.

[11] Patent Number: 5,972,908
[45] Date of Patent: Oct. 26, 1999

[54] COLLAGEN-BASED COMPOSITION AND PROCESS FOR PREPARING IT

[75] Inventors: Dominique Motte, Jouxtens-Mezery, Switzerland; Isabelle Volle, Lyons, France

[73] Assignee: Laboratoire Cosmetique De Lecousse, Paris, France

[21] Appl. No.: 09/042,219

[22] Filed: Mar. 13, 1998

[30]  Foreign Application Priority Data

Mar. 13, 1997 [FR] France ..................................... 9703006

[51] Int. Cl.$^6$ ..................... A61K 38/39; A61K 31/715
[52] U.S. Cl. .................... 514/54; 514/18; 514/801; 514/844; 514/944
[58] Field of Search .................... 514/2, 18, 54, 514/844, 944, 801

[56]  References Cited

U.S. PATENT DOCUMENTS 3,632,350   1/1972   Battista ......................................... 99/1
4,131,650   12/1978  Braumer et al. ........................... 424/28

FOREIGN PATENT DOCUMENTS

| 188382 B | 6/1981 | Czechoslovakia . |
|---|---|---|
| 0 507 193 A1 | 3/1992 | European Pat. Off. . |
| 0 709 101 A2 | 5/1996 | European Pat. Off. . |
| 6652 M | 12/1966 | France . |
| WO 95/17428 | 6/1995 | WIPO . |

OTHER PUBLICATIONS

Lazarev, V. A. Byull. Eksp. Biol. Med., vol. 82(10): 1216–1218, 1976.
Tu et al. J. Amer. Leather Chem. Assoc., vol. 64(12): 598–613, 1969.

*Primary Examiner*—Howard C. Lee
*Attorney, Agent, or Firm*—Knobbe, Martens, Olson & Bear, LLP

[57]  ABSTRACT

This process for preparing a collagen-based composition, comprises grinding collagen fibers to a particle size of between 10 and 100 microns and mixing them with water in a sufficient quantity to give a gel.

5 Claims, No Drawings

COLLAGEN-BASED COMPOSITION AND PROCESS FOR PREPARING IT

CROSS-REFERENCE TO RELATED APPLICATIONS

This application claims priority under 35 U.S.C. § 119 to French patent application No. 97 03006, filed on Mar. 13, 1997.

FIELD OF THE INVENTION

This invention relates to a collagen-based composition and a process for preparing it.

There are numerous formulations containing collagens of different types extracted from animals, mammals or fish, for the purpose of contributing to skin care.

The range of cosmetics available includes skin care, beauty and hygiene products in liquid or paste form containing collagen.

There are also lyophilized collagen masks or face-packs intended for use on the skin, both for therapeutic and cosmetic purposes.

More elaborate preparations are also available, such as films, beads and powders containing collagen for more medical applications.

The processes for producing collagen are widely known, i.e., it is obtained from animal dermis, which is ground, then treated in an acid solution and the soluble fraction of the collagen is extracted. In some cases it is useful to obtain fibers. From these fibers, which are gelatinized, masks are obtained by lyophilization. Similarly, by crosslinking the soluble fraction of the collagen, it is also possible to obtain films, masks or face-packs by lyophilization.

EP 0 709 101 describes the preparation of a heat-stable gel based on collagen which has to be dissolved at 50° C. with very rapid stirring (turbo-stirrer). This gel is an industrial preparation sold as it is.

All these forms of collagen-based composition require lyophilization for their production and are therefore expensive.

DETAILED DESCRIPTION OF THE INVENTION

The invention overcomes these disadvantages with a process for preparing a collagen-based composition which is much simpler to carry out than before and, as a result, much less expensive.

The process consists of grinding collagen fibers to a particle size of between 10 and 100 microns and mixing them with water and, optionally, a polysaccharide, in a sufficient quantity to produce a gel. In this way, a collagen-based composition in the form of a gel is obtained, comprising 1 to 2 parts by weight of collagen and, correspondingly, 99 to 98 parts of water.

Unexpectedly, it has been found that, when collagen fibers ground to the particle size indicated are brought into contact with water, especially at ambient temperature (4 to 28° C.) simply by stirring by hand, in less than 15 minutes a gel is formed, the viscosity of which, notably between 8000 and 80,000 cps, as measured at ambient temperature with a Brookfield module 5 viscometer, is sufficient to allow the immediate formation of a collagen-based mask which may be used for cosmetic or therapeutic purposes.

Preferably, 0.1 to 0.8 parts by weight of polysaccharide, which may preferably be a gum such as guar gum or xanthan gum, are added to the collagen, the polysaccharide constituting 10 to 40% of the weight of the collagen fibers.

The product is preferably sold in two pots, one containing the collagen fibers, optionally with polysaccharide added thereto, and the other containing water. The user does not mix the contents of the two pots together until the moment he is ready to prepare the mask, so that the prepared gel is fresh and its ingredients do not separate over time.

The first step of the process consists of grinding animal collagen fibers, from mammals or fish, to the required particle size. The fibers used may be obtained, in known manner, by treating the raw materials with soda or in the presence of enzymes such as pepsin. To reduce them to the required particle size, they may be ground with a blade-type grinder. It is also possible to use the freeze-grinding method using liquid nitrogen, for example. This step may be carried out in the factory.

The second stage of the process which may be carried out at the user's home, at any time, consists of adding water to this powder. If desired, before the water is added, the fine powder may be mixed with polysaccharides which will participate in the rapid and homogeneous gelatinization of the powder. The quantities of polysaccharides used will be between 10 and 40% of the weight of the fibers used, preferably 20%; ideally, these polysaccharides are added to the collagen fibers in the factory.

The finished powder may include active principles which will be released on the skin as they are rehydrated, during the skin care procedure. These water-soluble active principles are selected from the soluble vitamins, the oligo-elements, and plant extracts such as saponins, for example. These additions may vary depending on the purpose intended by the person formulating or preparing the product.

Depending on the active principles, the composition may be protective, maintaining normal skin function or improving the skin by moisturizing it, for example. It may treat aesthetic problems such as redness or dermatological problems such as acne, erythema or hematoma, in particular.

The following Examples illustrate the invention:

EXAMPLE 1

Obtaining 100 grams of gelatinizable powder 1 kg of dermis from a calf less than 6 months old is used as starting material.

The dermis is converted into fibers by known methods, e.g., by pre-treatment with soda followed by precipitation with sodium chloride at an acid pH, removing the salt and drying the precipitate by repeated bathing with acetone.

Some 85 grams of dried fibers are obtained, which are freeze-ground under liquid nitrogen introduced directly into the grinder.

1 liter of nitrogen is needed for this operation.

The powder has a mean particle size of 50 $\mu$m.

80 g of finely ground powdered fibers are obtained, which are mixed with 20 g of JAGUAR® gum made by Rhone-Poulenc, based on guar gum.

1 gram of this powder is gelatinized by the addition of 99 ml of water.

This preparation in the form of a gel can be used in a cubicle to cover the face or the part of the body to be treated.

EXAMPLE 2

Obtaining powdered fish collagen or marine collagen as in Example 1.

This is obtained from the skin of soles, which are warm-water fish, thus providing improved heat resistance, by grinding the sole skins, washing with phosphate-buffered solution, enzyme treatment with pepsin, precipitation with NaCl at a pH below 5, successive washes with a 50/50 water/acetone mixture, drying in an oven and freeze-grinding as in Example 1. The yield is 10%. 1 to 2 g of this powder are gelatinized with 99 to 98 ml of water.

EXAMPLE 3

Peelable masks. These are made by adding 2 g of cellulose fibers to the powder in Example 1.

EXAMPLE 4

To the gel obtained in Example 1 or 2 are added saponins obtained from lesser celandine, in a quantity of 2% by weight of gel. The product obtained is designed to combat sun damage to the skin.

EXAMPLE 5

Using the same initial method as in Example 4, but with 5% of an arnica spray instead of the saponins, a gel is obtained which is intended for decongesting a hematoma.

EXAMPLE 6

The powder is gelatinized with a 5% aqueous aloe extract; this preparation is used for moisturizing the skin.

EXAMPLE 7

Designing an "anti-aging" formula:

The following active extracts are added to the basic formulation in Example 1 or 9:

2% of marine elastin 0.08% of hyaluronic acid 0.5% of water-soluble vitamins

2% of Ginkgo biloba

EXAMPLE 8

Designing a formula for "diffuse redness":

Plant extracts are added to the basic formulation in Example 1 or 9:

3% of extract of Centella asiatica

2% of extract from a plant of the genus Ruscus 1.5% of extract from a plant of the genus Hydrastis

EXAMPLE 9

Example 1 is repeated, but without the addition of gum.

A gel is obtained which can be used to cover the face.

We claim:

1. A process for preparing a collagen-based composition, comprising grinding collagen fibers to a particle size of between 10 and 100 microns and mixing them with water in a sufficient quantity to give a gel.

2. The process of claim 1 comprising mixing 1 to 2 parts by weight of collagen fibers and 99 to 98 parts of water.

3. The process of claim 1 comprising mixing 0.1 to 0.8% parts by weight of polysaccharides with the collagen fibers.

4. A kit for preparing a gel, which comprises, in a first pot, 99 to 98 parts by weight of water and, in a second pot, 1 to 2 parts by weight of collagen fibers of a particle size of between 10 and 100 microns.

5. The kit for preparing a gel according to claim 4, wherein the second pot contains from 0.1 to 0.8 parts by weight of polysaccharides.

* * * * *